United States Patent
Wiygul et al.

(10) Patent No.: US 11,426,115 B2
(45) Date of Patent: Aug. 30, 2022

(54) SYSTEM AND METHOD FOR PELVIC FLOOR FEEDBACK AND NEUROMODULATION

(71) Applicant: Cornell University, Ithaca, NY (US)

(72) Inventors: Jeremy B. Wiygul, Ithaca, NY (US); Saie Milind Ganoo, Ithaca, NY (US); Rohit Curucundhi, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/486,859

(22) Filed: Sep. 27, 2021

(65) Prior Publication Data

US 2022/0007992 A1 Jan. 13, 2022

Related U.S. Application Data

(63) Continuation of application No. PCT/US2020/024960, filed on Mar. 26, 2020.
(Continued)

(51) Int. Cl.
| | |
|---|---|
| *A61B 5/391* | (2021.01) |
| *A61B 5/395* | (2021.01) |
| *A61B 5/296* | (2021.01) |
| *A61B 5/397* | (2021.01) |
| *A61B 5/313* | (2021.01) |
| *A61B 5/388* | (2021.01) |

(Continued)

(52) U.S. Cl.
CPC .......... *A61B 5/391* (2021.01); *A61B 5/0004* (2013.01); *A61B 5/227* (2013.01); *A61B 5/296* (2021.01); *A61B 5/313* (2021.01); *A61B 5/388* (2021.01); *A61B 5/395* (2021.01); *A61B 5/397* (2021.01); *A61B 5/6804* (2013.01); *A61B 5/7225* (2013.01); *A61B 5/7435* (2013.01); *A61N 1/36007* (2013.01); *A63B 23/20* (2013.01)

(58) Field of Classification Search
CPC ......... A61B 5/391; A61B 5/395; A61B 5/296; A61B 5/397; A61B 5/313; A61B 5/388; A61B 5/0004; A61B 5/227; A61B 5/6804; A61B 5/7225; A61B 5/7435; A61N 1/36007; A63B 23/20
See application file for complete search history.

(56) References Cited

U.S. PATENT DOCUMENTS

| | | | |
|---|---|---|---|
| 5,291,902 A | 3/1994 | Carman | |
| 6,264,582 B1 * | 7/2001 | Remes | A63B 23/20 600/595 |

(Continued)

FOREIGN PATENT DOCUMENTS

| | | | | |
|---|---|---|---|---|
| WO | 2018064172 A1 | 4/2018 | | |
| WO | WO-2018064172 A1 * | 4/2018 | ........... | A61B 5/0002 |

OTHER PUBLICATIONS

International Search Report and Written Opinion dated Aug. 12, 2020 in International Application No. PCT/US2020/024960.

*Primary Examiner* — Patrick Fernandes
(74) *Attorney, Agent, or Firm* — McDermott Will & Emery

(57) ABSTRACT

A computer-implemented method for pelvic floor feedback. The method includes capturing a strength of action potentials via wireless sensors, the wireless sensors positioned proximate to a pelvic floor of a user. The method also includes transmitting the strength of the action potentials to a mobile device. The method also includes recording the strength of the action potentials on the mobile device.

18 Claims, 12 Drawing Sheets

Related U.S. Application Data

(60) Provisional application No. 62/826,548, filed on Mar. 29, 2019.

(51) Int. Cl.
| | | |
|---|---|---|
| *A61B 5/00* | (2006.01) | |
| *A61B 5/22* | (2006.01) | |
| *A61N 1/36* | (2006.01) | |
| *A63B 23/20* | (2006.01) | |

(56) References Cited

U.S. PATENT DOCUMENTS

| | | | |
|---|---|---|---|
| 6,407,308 B1 * | 6/2002 | Roe | A61L 15/18 604/362 |
| 2016/0066836 A1 | 3/2016 | Schneider | |
| 2019/0192051 A1 * | 6/2019 | Savinen | A61B 5/486 |

* cited by examiner

SYSTEM AND METHOD FOR PELVIC FLOOR FEEDBACK AND NEUROMODULATION

CROSS-REFERENCE TO RELATED APPLICATION

The present application is a bypass continuation of International Application No. PCT/US2020/024960 filed on Mar. 26, 2020, which claims the benefit of priority under 35 U.S.C. § 119(e) to U.S. Provisional Patent Application Ser. No. 62/826,548, entitled "SYSTEM AND METHOD FOR PELVIC FLOOR FEEDBACK AND NEUROMODULATION," filed on Mar. 29, 2019, the disclosures of which are hereby incorporated by reference in their entirety for all purposes.

BACKGROUND

Electromyograph (EMG) biofeedback utilizes real time measurements of muscle contraction and relaxation via measurement of action potentials to allow a user to gain control over those muscles. EMG therapy has applications related to a large range of patient complaints, including neurologic and musculoskeletal pain, tension headaches, cerebral palsy, and urinary and fecal incontinence, in addition to many others.

Typically the equipment utilized to perform biofeedback has been an array of electrodes placed on the muscle group of interest, which are connected to a receiver or receiver type device that amplifies the signals from the muscles and presents it back to the patient in either an audio or visual signal. This equipment comes in a variety of forms, but the receiver is typically a multifunctional computer, which limits the application of EMG biofeedback in terms of space. In addition, the sensor electrodes must be placed by someone with training in EMG biofeedback, or the patient themselves must be taught to place them. Therefore, there is a need for EMG biofeedback equipment that overcomes these deficiencies.

The description provided in the background section should not be assumed to be prior art merely because it is mentioned in or associated with the background section. The background section may include information that describes one or more aspects of the subject technology.

SUMMARY

According to some implementations, a computer-implemented method provides for pelvic floor feedback. The method includes capturing a strength of action potentials via wireless sensors. The wireless sensors may be positioned proximate to a pelvic floor of a user. The method also includes transmitting the strength of the action potentials to a mobile device. The method also includes recording the strength of the action potentials on the mobile device.

According to some implementations, the method may also include capturing controlled contractions and relaxations of a target muscle group of the pelvic floor of the user. The method may further include comparing the controlled contractions and relaxations of the target muscle group with performance of other users. The method may further include comparing the controlled contractions and relaxations of the target muscle group with a previous performance of the user. The method may further include creating an online gaming environment via a remote server where a user may compete against other users interacting via other mobile devices connected to the remote server.

According to some implementations, a system provides for pelvic floor feedback. The system may include a memory storing computer-readable instructions and a processor. The processor is configured to execute the computer-readable instructions, which when executed carry out a method. The method includes capturing a strength of action potentials via wireless sensors. The wireless sensors may be positioned proximate to a pelvic floor of a user. The method also includes transmitting the strength of the action potentials to a mobile device. The method also includes recording the strength of the action potentials on the mobile device.

According to some implementations, the memory may also store computer-readable instructions, which when executed cause the processor to capture controlled contractions and relaxations of a target muscle group of the pelvic floor of the user. The memory may further store computer-readable instructions, which when executed cause the processor to compare the controlled contractions and relaxations of the target muscle group with performance of other users. The memory may further store computer-readable instructions, which when executed cause the processor to compare the controlled contractions and relaxations of the target muscle group with a previous performance of the user. The memory may further store computer-readable instructions, which when executed cause the processor to create an online gaming environment via a remote server where a user may compete against other users interacting via other mobile devices connected to the remote server.

According to some implementations, a device for pelvic floor feedback includes an adjustable housing comprising a garment or a saddle. The device also includes a plurality of sensors coupled to the housing, the plurality of sensors positioned at locations for facilitating pelvic floor neuromodulation and/or electromyograph (EMG) biofeedback with a user. The device also includes a transmitter coupled to the plurality of sensors through the housing, the transmitter comprising a Bluetooth Low Energy (BLE) device.

According to some implementations, the plurality of sensors are arranged in a sensor array comprising opposing pairs of sensor electrodes. The plurality of sensors may include at least one pair of elongated electrodes. Each electrode in the pair of elongated electrodes is between about 3.5" to about 4.5" long, and between 0.75" and about 1.25" wide. The plurality of sensors may be positioned in the housing, such that when the housing is mounted by a user, the sensors are positioned adjacent to a user's pudendal nerve and/or perineal nerve. The plurality of sensors may be included on a disposable flexible circuit comprising a polyethylene terephthalate (PET) substrate.

According to some implementations, the garment may include leg holes such that the plurality of sensors are located between the leg holes. According to some implementations, the transmitter may be coupled to a patient interface.

According to some implementations, the adjustable housing may include a bridge comprising at least one spring hinge. The saddle may include a pillow having a pressure to compress 25% of between 0.6 and 4.0 psi.

According to some implementations, the device may also include an amplifier configured to apply a neuromodulation signal to at least a subset of the plurality of sensors. The device may further include a multiplexer configured to select a set of the plurality of electrodes receiving the greatest magnitude electrical signal.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The disclosed systems, methods, and devices provide for the application of EMG-based biofeedback for tracking and treatment of a variety of muscular and neurologic disorders. Specifically, an EMG-based biofeedback system is designed to be used with widely available mobile computing devices for implementing a system of gamification to allow competition amongst treatment groups. By detecting and/or stimulating nerves and/or muscles around a patient's anal region and/or pudendal nerve, the patient may be trained to overcome associated muscular and neurologic disorders of those regions.

The disclosed systems, methods, and devices address a problem in traditional EMG biofeedback techniques, namely, the technical problem of application of EMG biofeedback to patients. The disclosed system solves this technical problem by providing for systems, methods, and devices that measure and provide improved EMG biofeedback. The disclosed subject technology further ensures proper placement of sensors in a portable solution, without the need for professional training.

Figure 1:
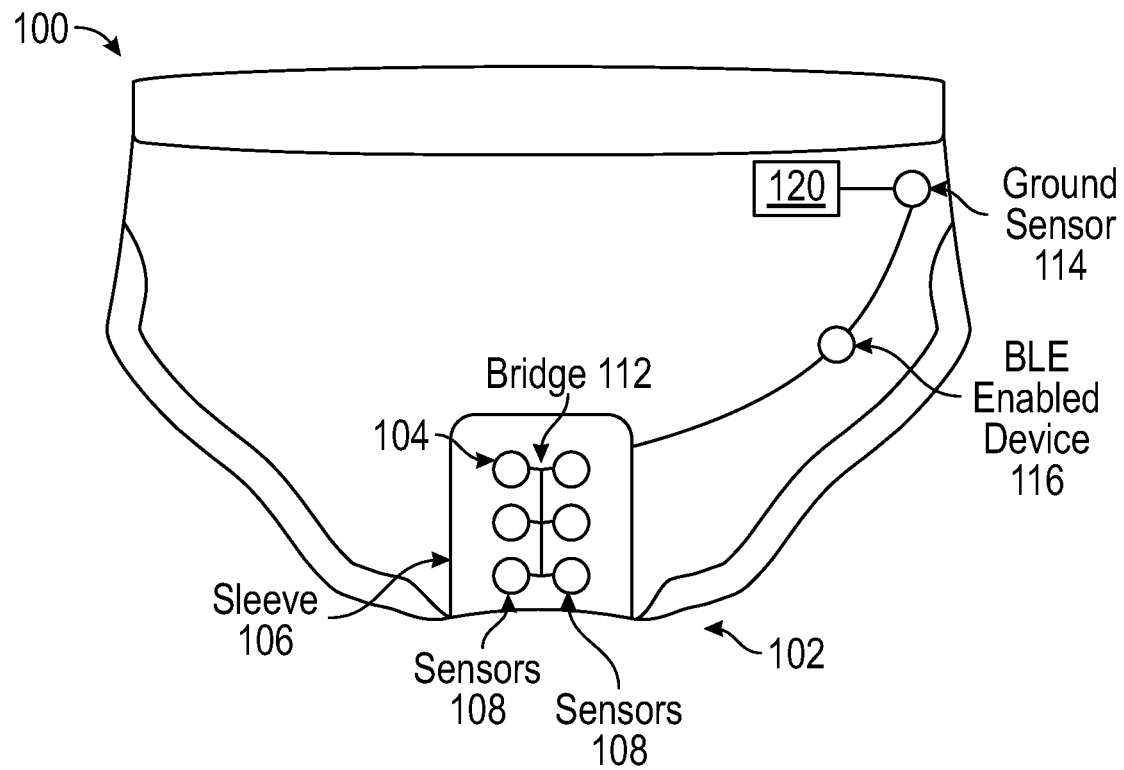
FIG. 1 is a back view of a garment with embedded technology for pelvic floor biofeedback, including a sensor array and spring action bridge within a sleeve, according to some implementations.
Figure 2:
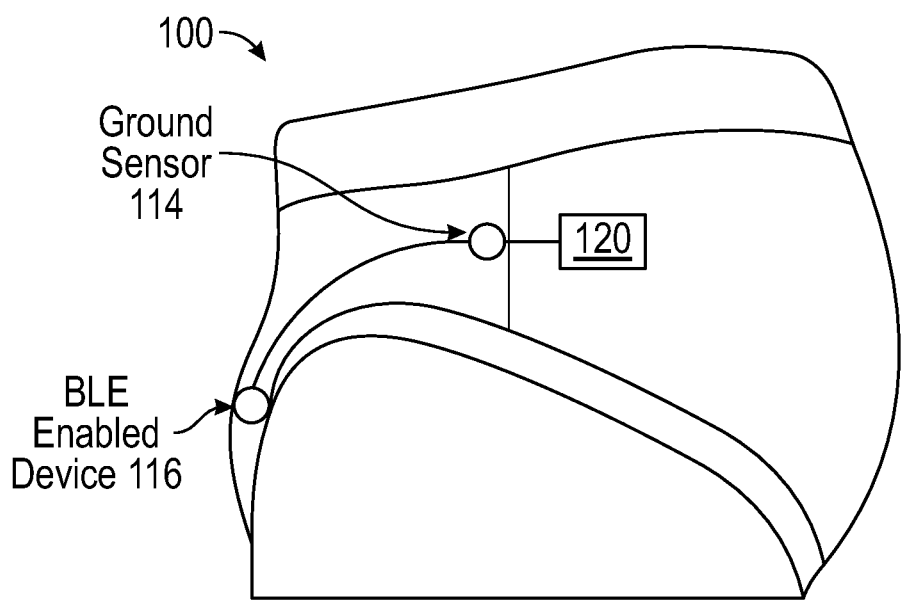
FIG. 2 is a lateral view of a garment with embedded technology for pelvic floor biofeedback according to some implementations.
Figure 3:
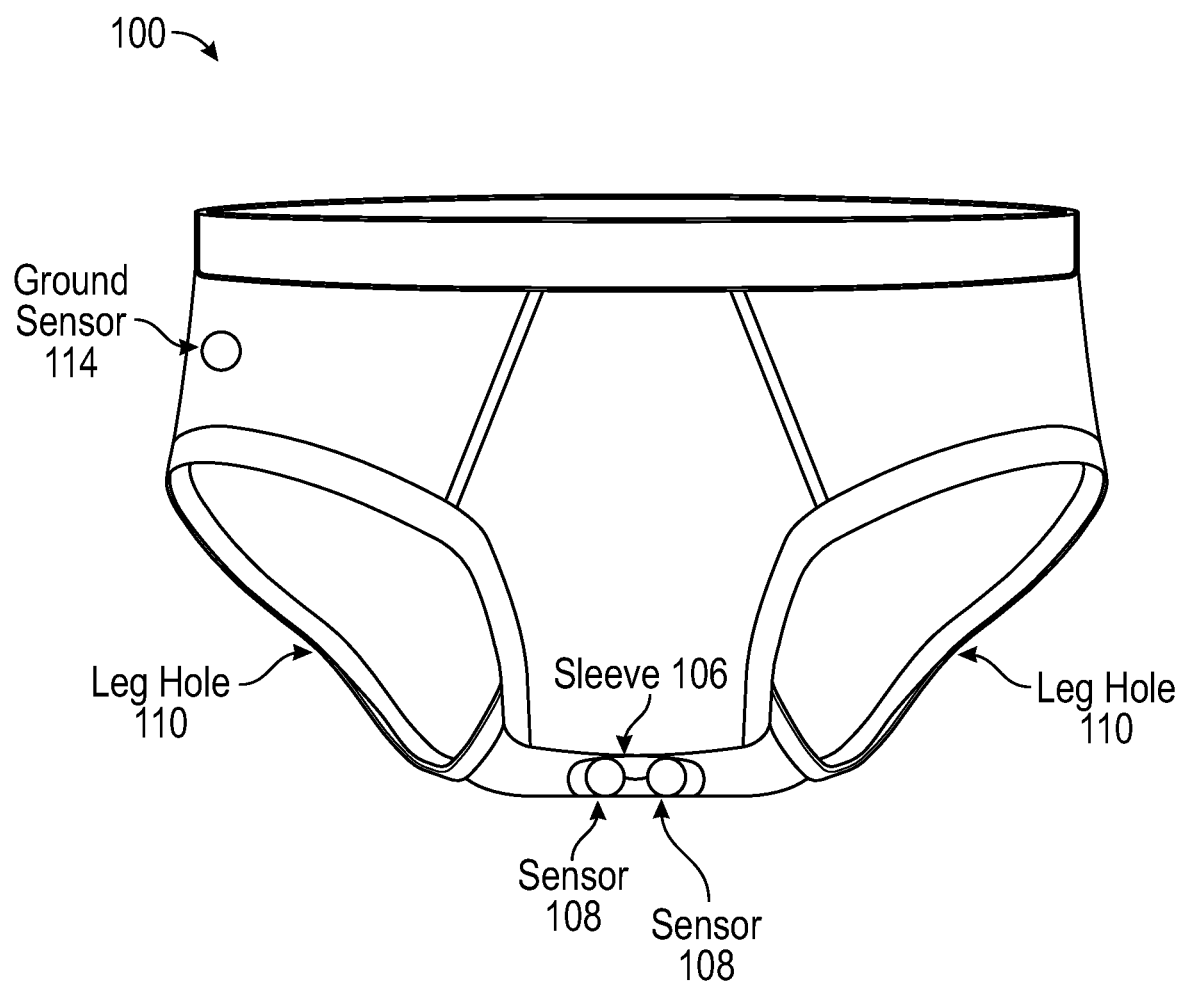
FIG. 3 is a front view of a garment with embedded technology for pelvic floor biofeedback, including a sensor array and spring action bridge within a sleeve, according to some implementations.

FIGS. 1-3 illustrate a garment 100 with embedded technology 102 for pelvic floor biofeedback, including a sensor array 104 with a spring action bridge 112 within a sleeve 106, according to some implementations. The sensor array 104 may include sensors 108 arranged in pairs along a longitudinal axis of the sleeve 106. For example, the sensor array 104 may be contained within the sleeve 106 between leg holes 110 of the garment 100.

The garment 100 may be worn on the lower part of a patient's body. The garment 100 may be adjustable to fit different users. The sleeve 106 may be specifically designed to allow the sensor array 104 to be inserted or sewn into the garment 100. For example, the sleeve 106 may be included along a central longitudinal axis of the garment 100 to allow proximate positioning of the sensor array 104 along the levator ani muscle group (e.g., urinary and fecal sphincters).

The garment 100 may be made of a mesh conductive material or may include conductive material inside of sensor pockets to allow for increased function of the sensors 108. For example, the conductive material may include silver/nylon fabric. The sensors 108 may be included within pockets to allow for specific targeting of various muscle groups local to the urinary and fecal sphincters. The mesh garment 100 may also include electrically non-conductive material, such as polyester, in desired locations to reduce detection from adjacent muscle groups.

The sensors 108 may be directly wired to a transmitter 116 within the garment. The sensors 108 may be configured to sense and/or modulate/stimulate muscle movement/contractions. The transmitter 116 may be configured to communicate wirelessly, such as via Bluetooth, to a mobile device. For example, in users undergoing pelvic floor biofeedback, the garment 100 could include mesh underpants with sensor pockets (e.g., sleeve 106) sewn near a center length, such that when the user puts them on, the sensors 108 may be positioned proximate to the anal sphincter or the pudendal nerve. A bridge mechanism 112 that causes the sensors 108 to be forced into the gluteal cleft, along the longitudinal axis of the levator ani muscle, may be included to improve sensor-skin contact. For example, the bridge mechanism 112 may be included within the sleeve 106 onto which the sensor array 104 is placed. The bridge mechanism 112 may include a spring that causes the sensors 108 to be forced into the gluteal cleft to improve contact of the sensors 108 with the skin of the patient. The garment 100 may further include a ground electrode 114 against which sensed electrical activity is compared.

In some implementations, the transmitter 116 may include a Bluetooth Low Energy (BLE) enabled device that is embedded in the garment 100 that receives muscle action potential data from the sensors 108 of the sensor array 104. The BLE enabled device may also receive and amplify signals from the wireless sensors 108 and interface with a mobile device via a BLE connection. For example, a downloadable software system on the mobile device may be configured to interact with the BLE device 116 within the garment to display the signals passed from the embedded sensors 108 onto the screen of the mobile device. In this way the patient may monitor results from the muscle groups of interest. A battery 120 may provide power to the electrical elements of the garment 100.

Figure 4:
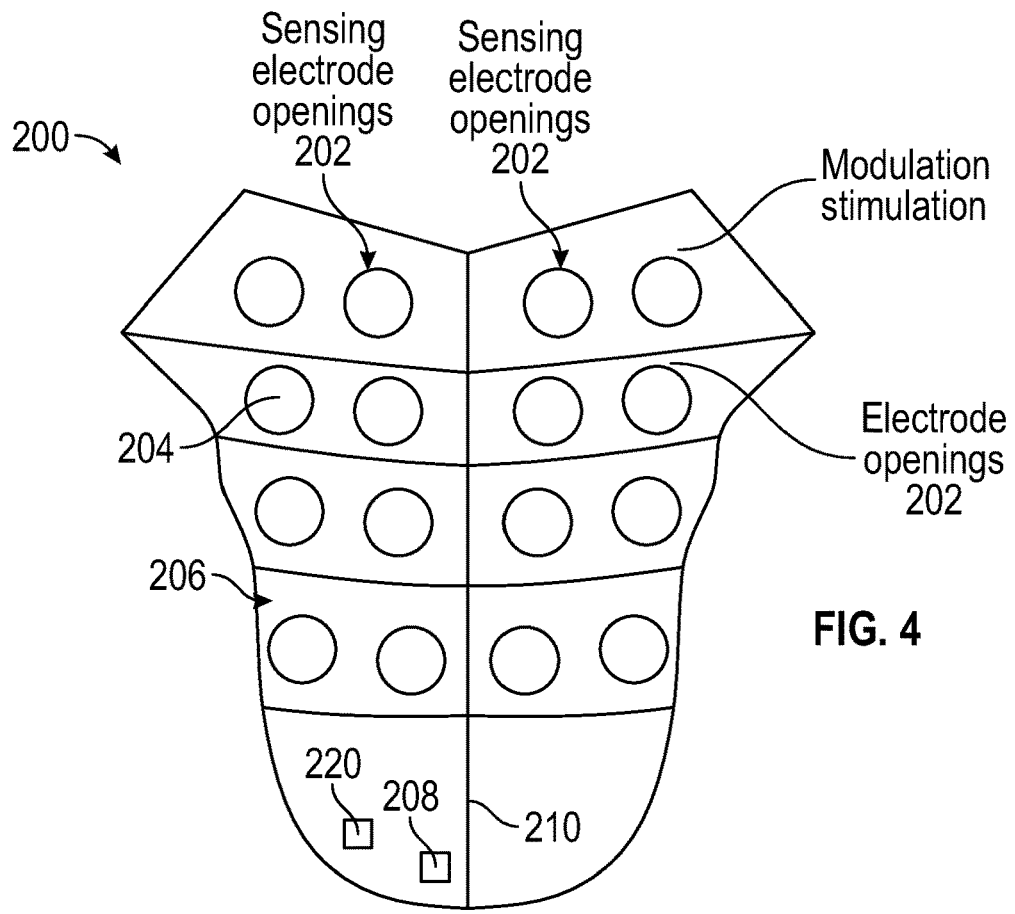
FIG. 4 is a top view of saddle with locations for placement of a sensor array according to some implementations.
Figure 5:
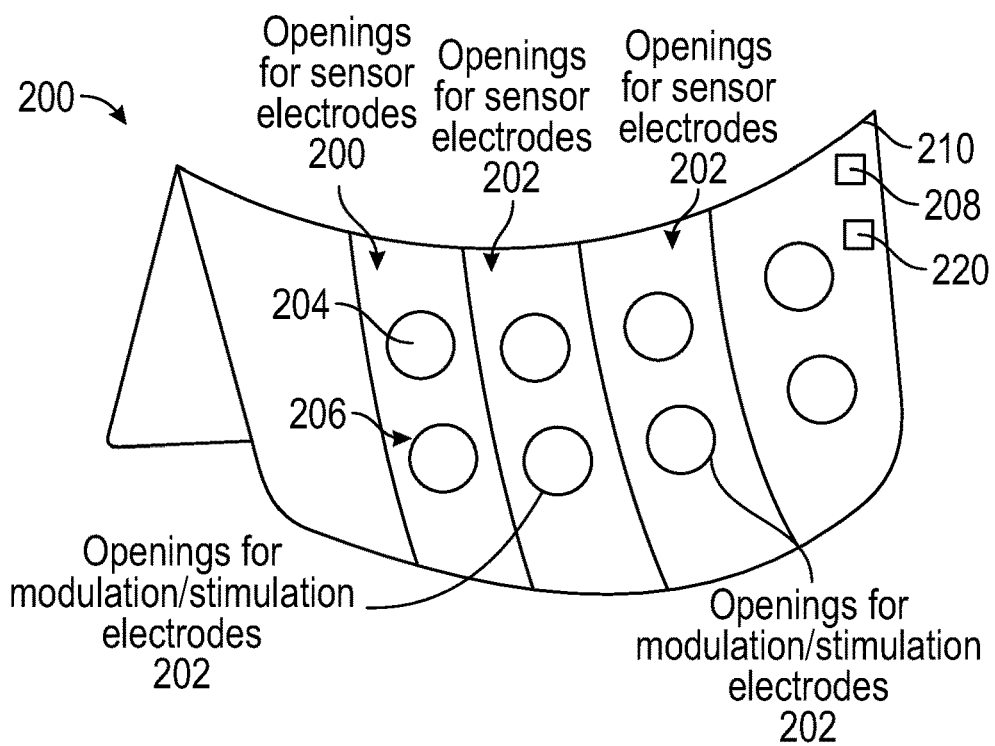
FIG. 5 is a side view of saddle with locations for placement of a sensor array according to some implementations.
Figure 6:
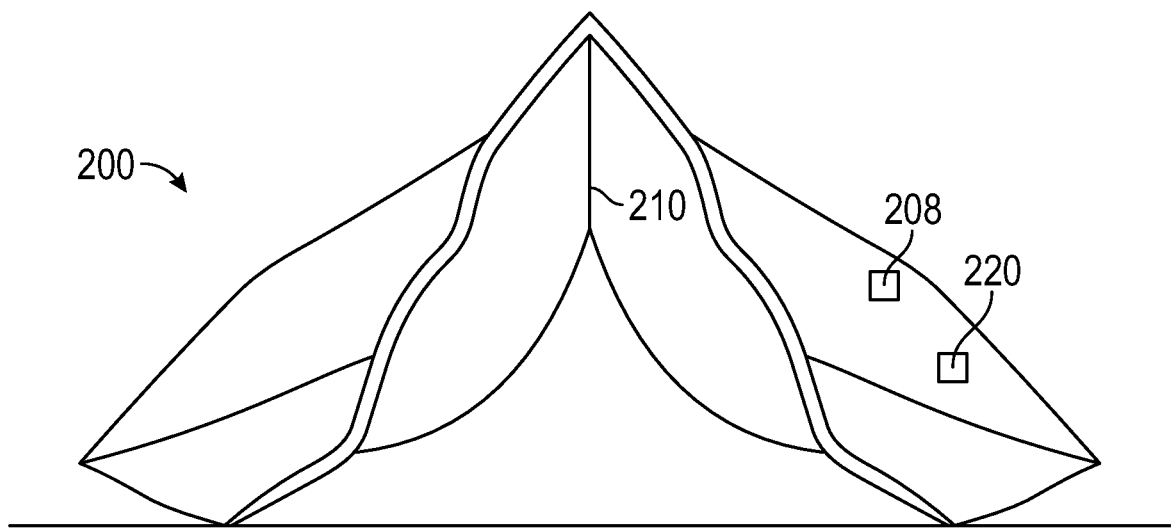
FIG. 6 is a front view of saddle according to some implementations.

FIGS. 4-6 illustrate a saddle 200 with positions 202 of a sensor array 206 according to some implementations. The saddle 200 may be configured to be sat upon by a patient, such that the patient's urinary and fecal sphincters are in contact with the sensors 204 of the sensor array 206. The saddle 200 may be adjustable to fit different users. Similar to the garment 100 described above, the saddle 200 may be made of a mesh conductive material or may include conductive material inside of sensor pockets 202 to allow for increased function of the sensors 204. For example, the conductive material may include silver/nylon fabric. The sensors 204 may target various muscle groups local to the urinary and fecal sphincters. The mesh garment 100 and saddle 200 may also include electrically non-conductive material, such as polyester, in desired locations to reduce detection from adjacent muscle groups.

The sensors 204 may be configured to sense and/or modulate/stimulate muscle movement/contractions. The sensors 204 may also be directly wired to a transmitter 208 coupled to the saddle 200. As illustrated, the transmitter 208 may be located at various locations on the saddle 200. The transmitter 208 may be configured to communicate wirelessly, such as via Bluetooth, to a mobile device. The saddle 200 may also include sensors 204 embedded within the upper surface of the saddle 200, on which the patient sits during treatment. The saddle 200 may also include a bridge 210 that facilitates contact of the sensors with the gluteal cleft and along the longitudinal axis of the levator ani muscle. A battery 220 may provide power to the sensors 204 of the saddle 200.

Figure 7:
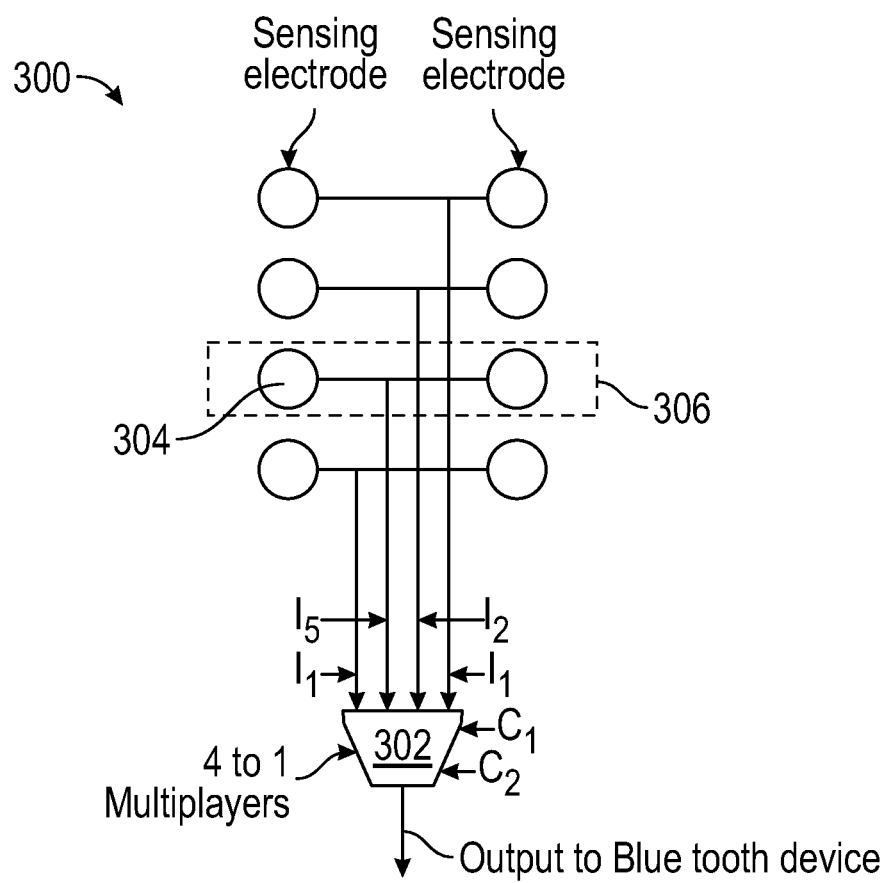
FIG. 7 is a schematic diagram of a sensor array with outputs connected to a multiplexer, according to some implementations.

FIG. 7 is a schematic diagram of a sensor array 300 (e.g., sensor array 104) with outputs connected to a multiplexer 302, according to some implementations. For example, the multiplexer 302 may be coupled output signals of multiple sensors 304, which may be contained within the garment 100 or saddle 200 of FIGS. 1 and 2. As illustrated, the garment 100 and the saddle 200 include locations for sensors 108, 204. It is understood that the sensor array 300 may be located at these locations. The multiplexer 302 may also include an output signal connected to a Bluetooth enabled device (e.g., transmitter 116) embedded in the garment 100 or saddle 200.

In some implementations of the present disclosure, the multiplexer 302 may include a 4 to 1 multiplexer having four inputs and one output. The multiplexer 302 may also include inputs for c1 and c2 inputs (e.g., control signals). In some embodiments, the multiplexer 302 may have any number of other inputs, for example up to 8 or 16 inputs, with one output, or in some implementations multiple outputs.

In some implementations of the present disclosure, the sensor array 300 may include pairs of electrodes 306. For example, each pair of electrodes 306 may include two sensors 304, which may be coupled to an input of the multiplexer 302. Each pair of electrodes 306 may be configured to sense and/or modulate/stimulate muscle movement/contractions. The pairs of electrodes 306 may be arranged in series. The multiplexer 302 is configured to select for output from the received input signals, the signal having the greatest amplitude. It is assumed that this greatest amplitude is due to the closest proximity to the desired tissue to be monitored. Each electrode may be generally circular in shape (though other regular or irregular shapes may also be used) with a diameter of between about 0.75" and 1.25", e.g., 1.0". The distance between opposing electrodes across the linear axis of the sensor array may range from about 0.75" to about 1.5", e.g., 1.0".

Figure 8:
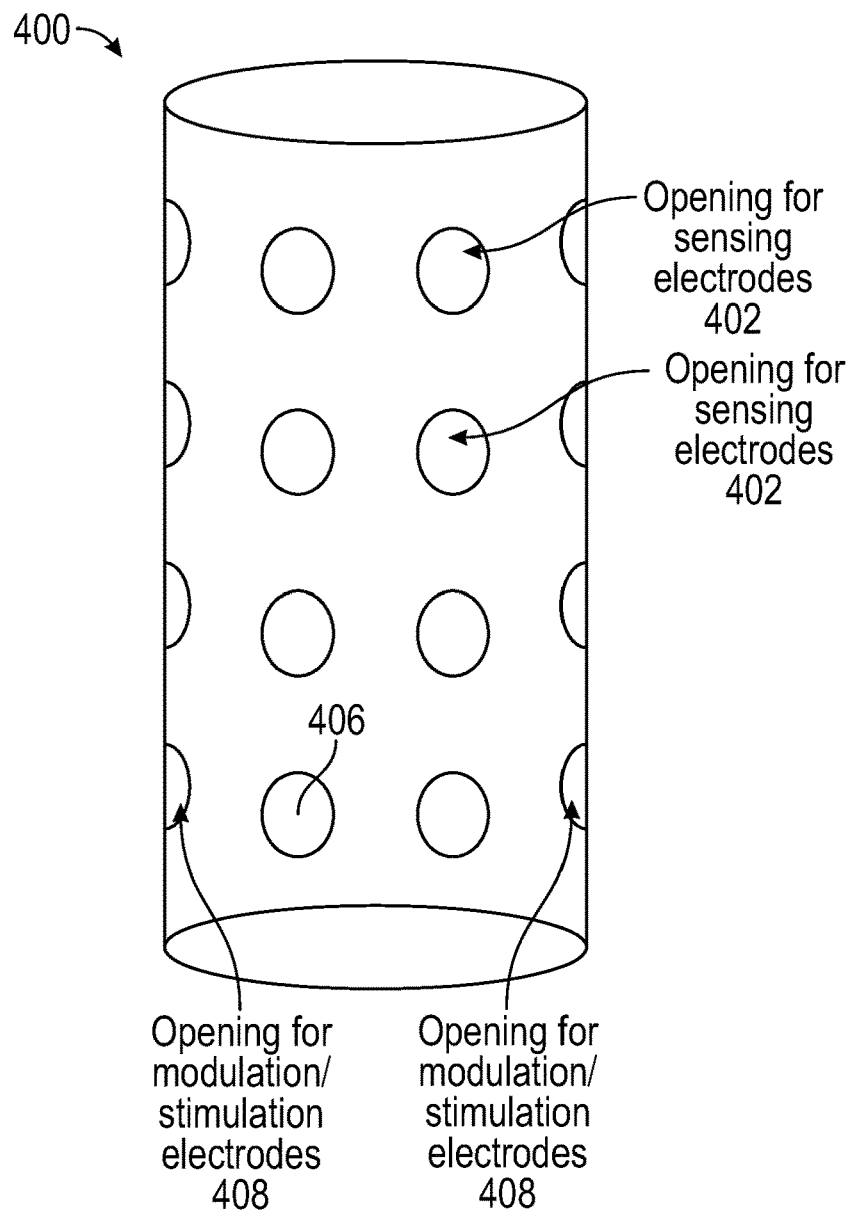
FIG. 8 is a top view of an alternative configuration of a saddle with positions of a sensor array, according to some implementations.
Figure 9:
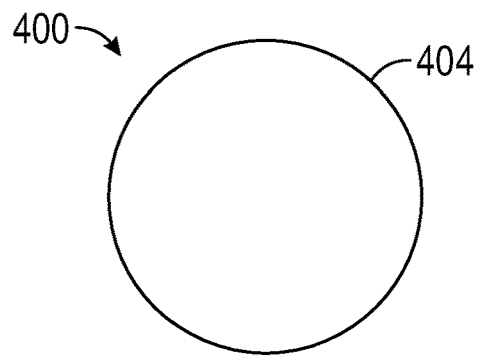
FIG. 9 is an end view of an alternative configuration of a saddle according to some implementations.
Figure 10:
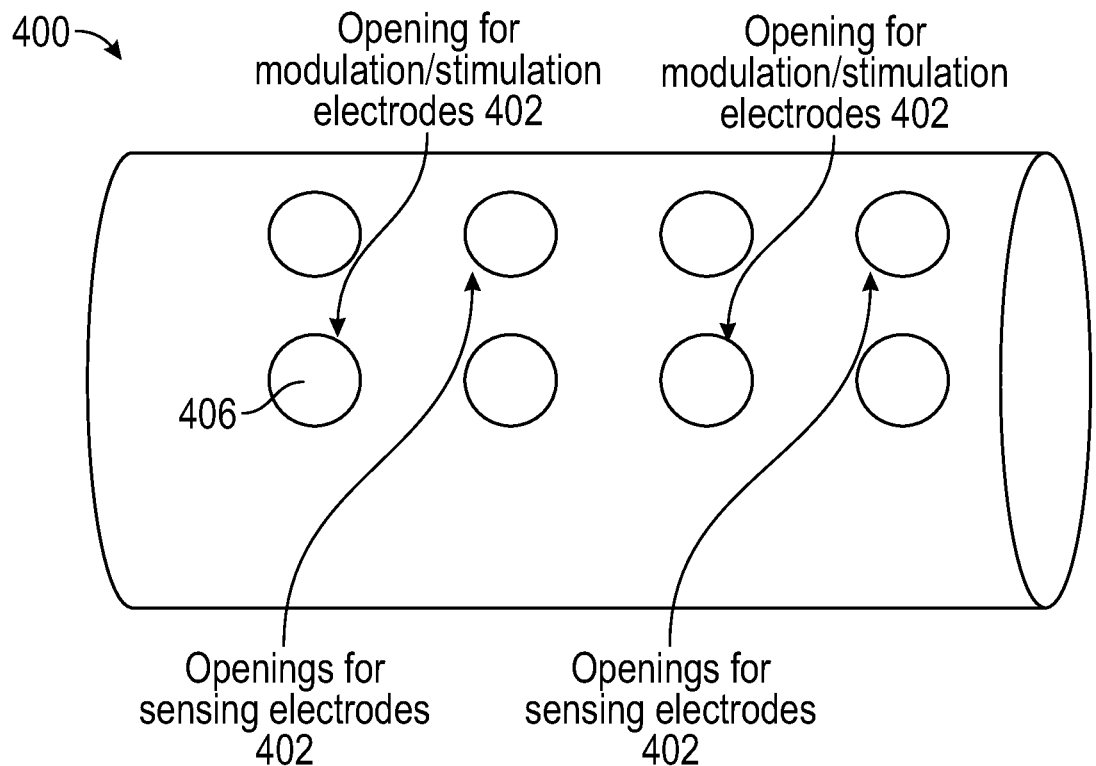
FIG. 10 is a side view of an alternative configuration of a saddle with positions of a sensor array, according to some implementations.

FIGS. 8-10 illustrate an alternative configuration of a saddle 400 (e.g., a pillow) with positions of a sensor array 402 (e.g., sensor array 104), according to some implementations. For example, the saddle 400 may be cylindrical in shape, with a circular cross-section (as shown in FIG. 9). The saddle 400 may include positions for a sensor array (e.g., openings for sensing electrodes 402, openings or modulation stimulation electrodes 408). The sensor array may include the above-described sensor array 104 in FIGS. 1-7. The positions 402, 408 may be located evenly around a circumference 404 of the saddle 400, as illustrated in FIGS. 8 and 10. The sensors 406 of the sensor array may be configured to sense and/or modulate/stimulate muscle movement/contractions.

According to some implementations of the present disclosure, the saddle 400 may include depressions for facilitating contact between target areas of the user's anal and perineum regions and the sensors 406. It is understood that the saddle 400 may be configured in shapes other than a cylinder. According to some implementations the saddle 400 may be integrated into a seat of an exercise bicycle, stool, or other such similar structure upon which a user can sit.

According to some implementations, the electrodes 406 may come in one multiple pairs to take into account, e.g., by combining sensed electrical activity, on both sides of the longitudinal axis of the sensor array. Multiple pairs can be provided as the locations of the respective sensor pairs relative to the patient's anatomy may be different each time the patient sits on the saddle 400 or when the patient shifts position while sitting on the saddle 400. Due the imprecision of relative electrode placement over time, the multiple pairs ensures that at least one electrode pair is sufficiently close to the desired monitoring location on the patient's anatomy to detect a relevant signal. Pairing the electrodes also provides improved coverage over the patient's pelvic floor. In alternative implementations, for example, shown in FIG. 16, described below, a single pair of elongated electrodes can be used to detect electrical activity originating along a longer region of the user's pelvic floor, reducing the need for multiple electrode pairs and a multiplexer. According to some implementations, the electrodes may also include modulation/stimulation electrodes, and or sensing electrodes. Placement of the modulation/stimulation electrodes may be different than placement of the sensing electrodes, as illustrated in FIGS. 1-10.

Figure 11:
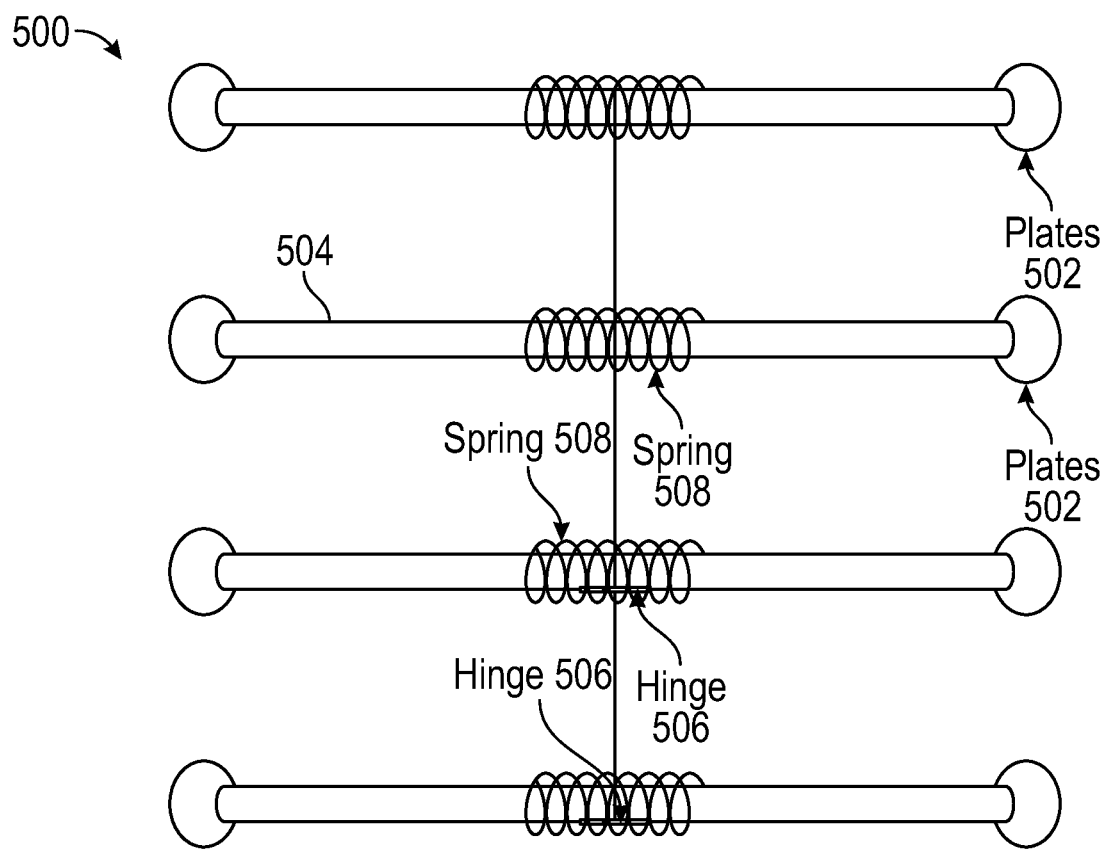
FIG. 11 is a bottom view of a bridge spring mechanism with plates for sensors, according to some implementations.
Figure 12:
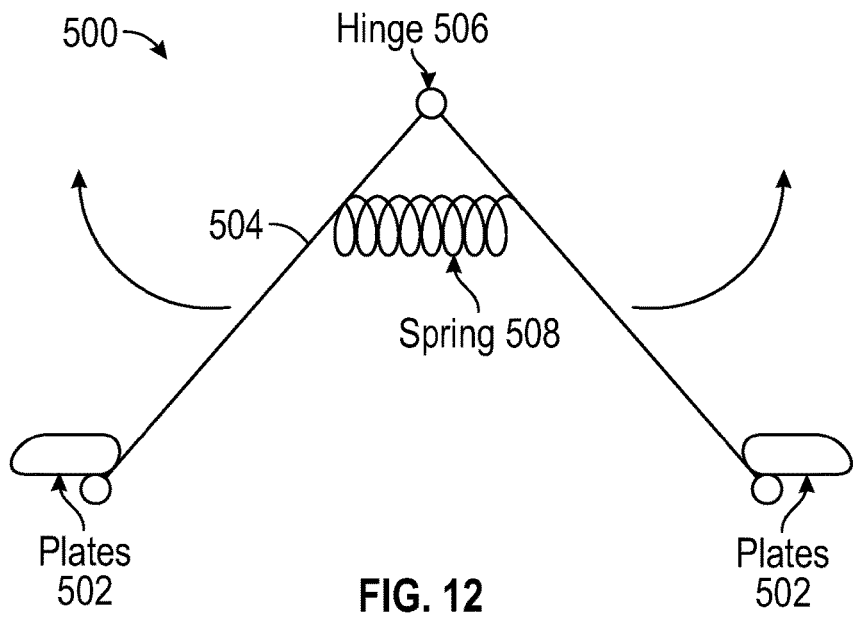
FIG. 12 is an end view of a bridge spring mechanism, demonstrating movement of arms of a bridge hinging away from a spring mechanism, according to some implementations.

FIGS. 11 and 12 illustrate a bridge spring mechanism 500 with plates 502 for applying distributed pressure to the inner surface of the substrate into which the electrodes are coupled, according to some implementations. For example, the bridge spring mechanism 502 may include arms 504 with hinges 506. The plates 502 are located at the ends of the arms 504. The arms 504 may be forced towards a substantially straight position by springs 508 at the hinges. The arms 504 may be bent towards one another by a bending force, with the spring 508 producing a force opposite to the bending force. For example, the bending force may be applied by a user's buttocks, with the spring 508 opposing the bending force (as illustrated in FIG. 12), thus allowing the arms 504 and plates 502 to push the sensor array against the user's buttocks. It is understood that the illustrated bridge spring mechanism 500 is exemplary only, and other spring mechanisms may be utilized to achieve a substantially similar effect. It is further understood that sensors having the illustrated bridge spring mechanism 500 may be included with the sensor array of FIG. 7 for inclusion in a garment 100, for example.

Figure 13:
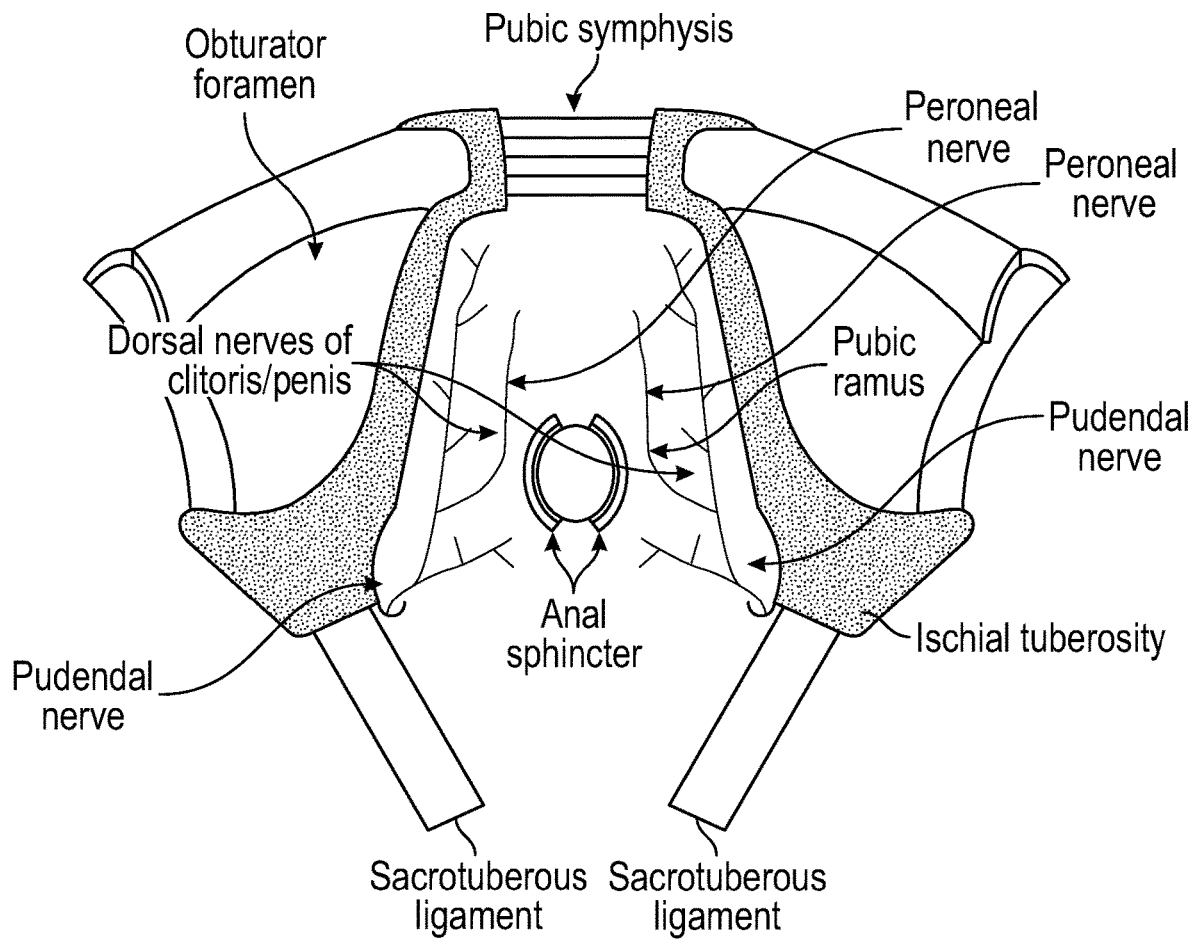
FIG. 13 is a diagram illustrating exemplary nerves, muscles, and ligaments with which aspects of the present disclosure may be implemented.
Figure 14:
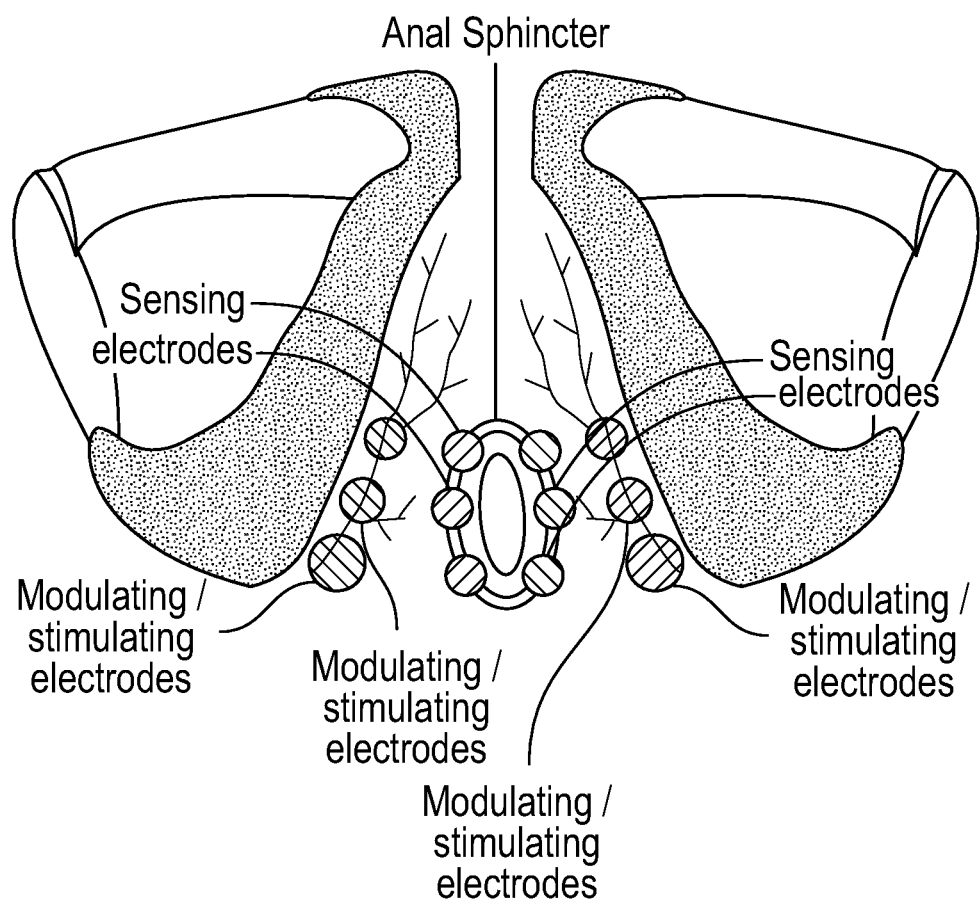
FIG. 14 is a diagram illustrating deployment of electrodes on exemplary nerves, muscles, and ligaments according to some implementations.

FIG. 13 illustrates various parts of a patient's anal region, which may be stimulated and/or monitored by the above-described sensors. FIG. 14 illustrates an exemplary placement of sensors proximate to a patient's anal region, specifically on the anal sphincter and pudendal nerve of the patient. It is understood that sensors may be placed proximate to other locations as well to provide stimulation and feedback, such as the perineal nerve.

According to some implementations of the present disclosure, the sensors may include sensing electrodes and modulating/stimulating electrodes. For example, the sensing electrodes may be grouped together and the modulating/stimulating electrodes may be grouped together. As illustrated in FIG. 14, the sensing electrodes may be positioned proximate to the anal sphincter for detection of anal sphincter contraction and relaxation. The modulating/stimulating electrodes may be positioned proximately along the pudendal nerve for modulating/stimulating the pudendal nerve. It is understood that the sensing and modulating/stimulating electrodes may be positioned according to a desired effect on a patient. For example, the modulating/stimulating electrodes may stimulate an effect to be sensed by the sensing electrodes. In this way, the sensing and modulating/stimulating electrodes may work together to achieve a desired result.

According to some implementations, stimulation of the pelvic floor may provide desired therapeutic effects by stimulating the nerves therein. Stimulation may also allow the patient to learn how to control the nerves better. In some implementations, the same electrodes that provide stimulation can also be used for sensing. In some implementations, sensors include dedicated stimulation electrode pairs and dedicated sensing electrode pairs. Such pairs may be in line with one another or staggered to fit more tightly together.

Figure 15:
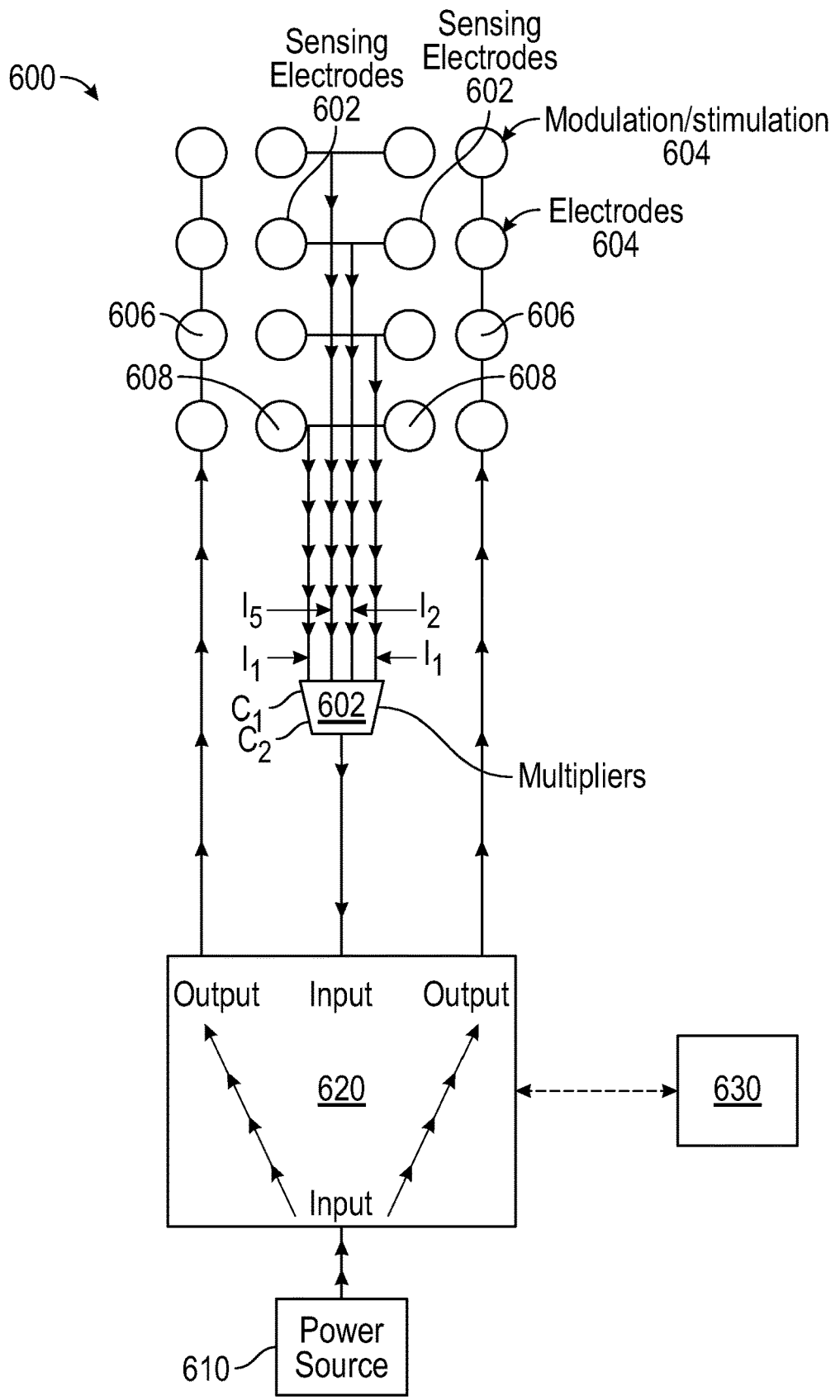
FIG. 15 is a schematic diagram of a sensor array with outputs connected to a multiplexer, according to some implementations.

FIG. 15 is a schematic diagram of a sensor array 600 with outputs connected to a multiplexer 602, according to some implementations. For example, the sensor array 600 may include sensing electrodes 604 coupled to inputs of the multiplexer 602, similar to the above-described configuration of FIG. 7. An output of the multiplexer 602 may be coupled to an input of a Bluetooth enabled device 620. It is understood that the sensor array 600 may be included in the marked sensor locations on the garment 100 or saddle 200, 400.

In some implementations of the present disclosure, modulation/stimulator electrodes 604 may be coupled to outputs of the Bluetooth enabled device 620. For example, the modulation/stimulator electrodes 604 may be arranged in pairs 606, which are coupled in series or in parallel to one another. In a sensing mode of operation, the sensing electrodes 602 detect signals emitted by the patient. The signal with the greatest magnitude is in turn relayed by the Bluetooth enabled device 620 to a processer (e.g., a mobile device, computer, etc.). The processor processes the signals and causes the Bluetooth enabled device 620 to apply a stimulation signal to a given pair 606 of the modulation/stimulator electrodes 604 to provide a desired effect on the patient based on the received input. The pair of electrodes 606 to which the stimulation signal is applied can be selected based on detecting a pair of sensors 608 receiving a highest signal amplitude while in a detection node. Alternatively, the stimulation signal may be applied to all electrode pairs 606, 608. The Bluetooth enabled device 620 may be powered by a power source 610, such as a rechargeable battery.

In some implementations, the Bluetooth enabled device may be coupled to a server 630 (e.g., a remote server coupled to a user's mobile device). For example, software for controlling the array 600 may be installed on the server 630. In an implementation, multiple devices (e.g., mobile devices) may access the server 630 and interact with the server 630 simultaneously.

In some implementations, the sensor array 600 may include an array of 2N electrodes, where N equals any integer greater than 0 that are coupled to a multiplexer 602. The multiplexer 602 may select the strongest of the signals coming from the sensor pairs 608. The output signal of the multiplexer 602 may be coupled to a preamplifier. An analog signal from the preamplifier may be sent to an analog-to-digital converter (ADC). In an implementation, the digital signal is sent to a mobile device such as a laptop computer installed with a software program. For example, the software program captures the digital signal in real time and displays the signal on a display (e.g., a screen). For example, the sensor array 600 may have 12 total electrodes (e.g., 6 pairs). The electrodes may be equidistant from a midline of the sensor array 600. According to some implementations, the sensor array 600 may include electrodes that are 5 mm to 10 mm in diameter and separated by 4-5 cm across the longitudinal axis of the array 600. In some implementations, the electrode separation distance may vary based on the size of the patient the sensor array is intended for. For example, more slender users may use a sensor array with electrodes that are spaced less far apart, whereas larger framed users, may use sensor arrays with more distantly spaced electrodes to accommodate their different anatomical features. Some implementations may include different numbers of electrode pairs, for example between 3 and 10 pairs. In some implementations, the distance between the electrodes of each pair of electrodes is the same. In some implementations, the distances vary, electrode pair-to-electrode pair.

Figure 16:
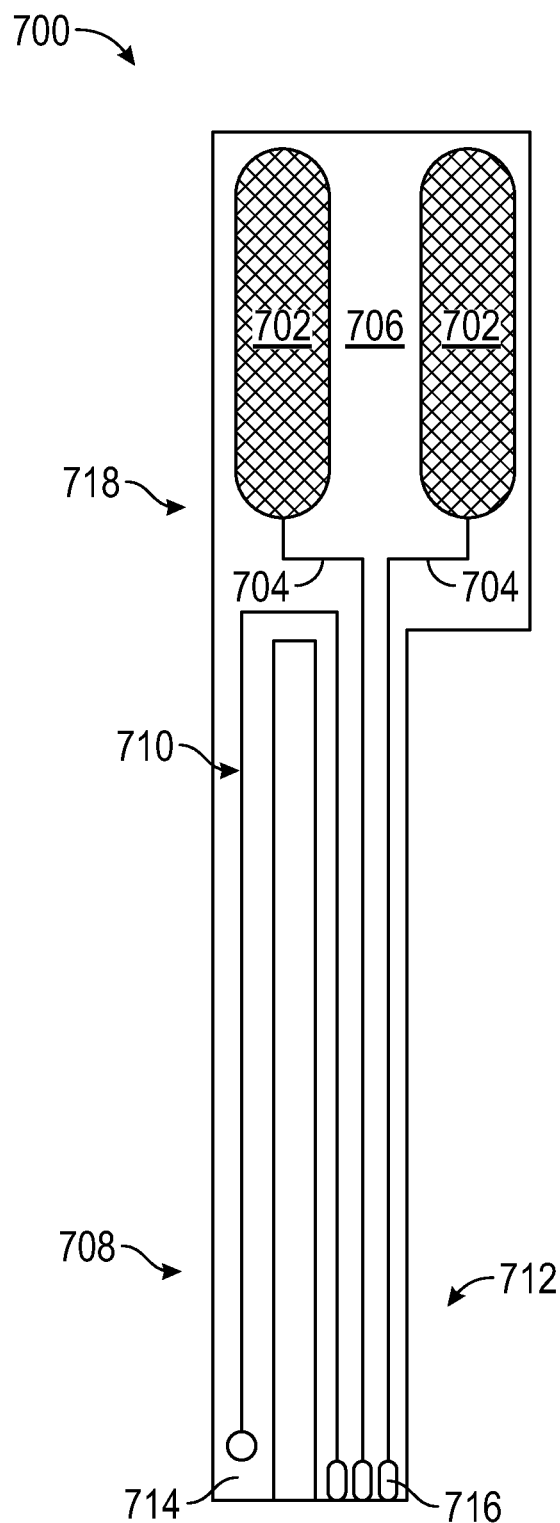
FIG. 16 is a diagram of a disposable flexible circuit, according to some implementations.

FIG. 16 is a diagram of a disposable flexible circuit 700, according to some implementations. For example, the circuit 700 may be included in any of the garment 100, saddle 200, 400 described above. The circuit 700 may include electrodes 702 coupled to traces 704 on a polyethylene terephthalate (PET) substrate 706. For example, the electrodes 702 may include the sensor arrays 300, 600 as described above. The traces 704 may extend from the electrodes 702 down an arm 712 of the circuit 700, such that the traces 704 couple the electrodes 702 to an edge connector 716. For example, the edge connector 716 may be 3×1, or otherwise.

The circuit 700 may further include a ground cable 708 having a ground trace 710 and an ECG snap connector 714. For example, the ground cable 708 may be configured to be bent upward to facilitate connection to a patient's device (e.g., such as a peel and stick ECG device, or other device).

Additionally, the longer single electrode pair 702 may ensure proximity to a user's nerves.

In an implementation, the circuit 700 may be single-sided (e.g., no traces on a back side of the circuit 700). In a further implementation, the electrodes 702 may be coated with an adhesive gel. According to some implementations, the traces 704 may be covered with a non-conductive coating (e.g., solder resist).

A back side of a rectangular portion 718 of the circuit 700 may be coated with an adhesive (e.g., a double-sided peel and stick adhesive) to facilitate temporary adhesion of the circuit 700 to a patient and/or a garment/saddle/pillow (e.g., garment 100 or saddle 200, 400, or otherwise). For example, the circuit 700 may be removed and disposed after use.

According to some implementations, dimensions of the electrodes 702 may be 1"×4". The electrodes 702 may also be spaced 1" apart from each other. In other implementations, the width of the electrodes may range from about 0.75" to about 1.25" and the lengths of the electrodes may range from about 3.5" to about 4.5" and they may be spaced between about 0.75" and 1.25" apart. According to some implementations, a dimension of the rectangular portion 718 may be 3.5"×5". In other implementations, the width of the rectangular portion may range from about 3" to about 4 inches and the length may range from about 4.5" to about 5.5". A dimension of the arm 712 may be 1"×10". In other implementations, the width of the arm may range from about 0.75" to about 1.25" and the length may range from about 8" to about 12". The dimensions of the ground cable 708 may be 0.75"×10". In other implementations, the length of the ground cable may be between 0.5" and 1.0" and the length may be between 8" and 12". It is understood that these dimensions are exemplary only. According to some implementations, the ground cable 708 and/or the arm 712 may be shortened and/or removed.

According to some implementations, the electrodes 702 may include circuit interconnects comprising silver ink. The electrodes 702 may be laminar in structure. For example, a base silver ink may be selectively applied to the substrate 706, followed by a gel of silver/silver chloride. In an implementation, the electrodes may be configured to provide a voltage range of 5V to 70V for stimulation.

According to some implementations, the circuit 700 may include an electrical connector for interconnecting to control electronics. In an implementation, interconnecting to the control electronics may be achieved via use of silver ink pads that engage an edge connector (e.g., edge connector 716).

According to some implementations, the circuit 700 may be coupled to a pillow. For example, the pillow may be shaped/configured similarly to the garment 100 or saddle 200, 400, or otherwise (e.g., cylindrical, bike seat shape, etc.). The pillow may have a stiffness similar to that of a memory foam pillow. According to some implementations, the pillow may have a compression rate (e.g., an amount of force that compresses a cubic foot of the material by 25%) that ranges in some implementations, from about 0.5 psi to about 5 psi, in some implementations from 0.6 psi to about 4 psi, or in some implementations from about 1 to about 2 psi. A diameter range of the pillow may be about 3"-5", for example, 4" or 7 cm, for example.

The pillow may include a circuit board including a battery (e.g., battery 120, 220, 610), a battery charger (e.g., included with the battery), a voltage regulator, an instrumentation amplifier for EMG signals, a microprocessor (and associated memory for program storage and data storage), a pre-amplifier and analog-to-digital converter, a wireless serial data transceiver (e.g., Bluetooth), a stimulation pulse generator, and/or patient isolation circuitry. In some implementations, some or all of the additional circuitry may be included in an application specific integrated circuit (ASIC) included on the disposable circuit 700.

Figure 17:
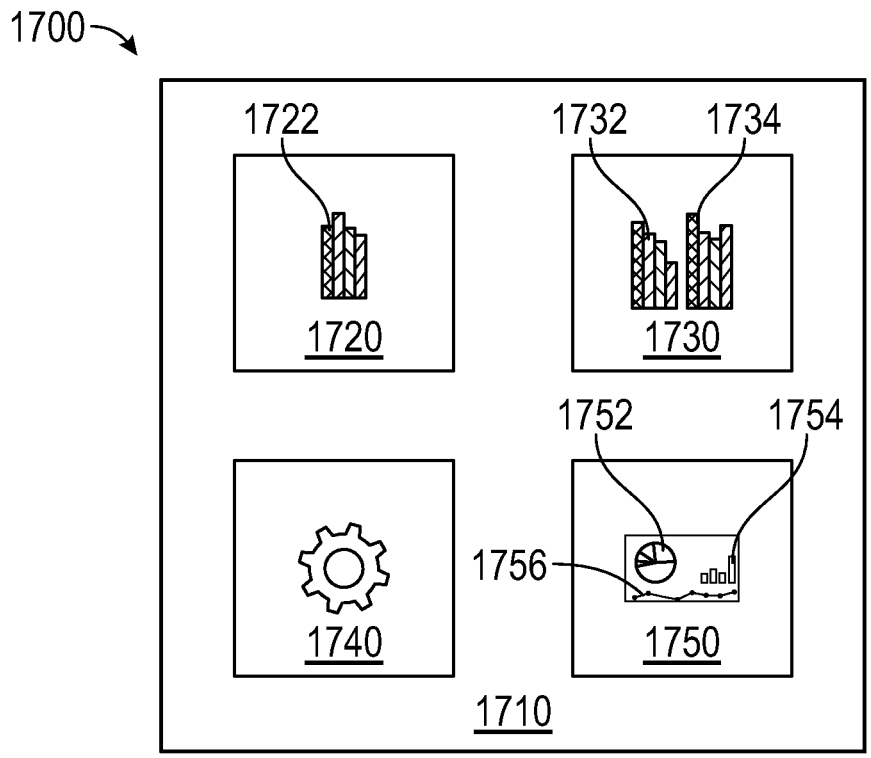
FIG. 17 is a diagram of an exemplary generated user interface (GUI) according to some implementations.

FIG. 17 is a diagram of an exemplary generated user interface (GUI) 1700 according to some implementations. For example, the GUI 1700 may be configured to interface with a Bluetooth enabled device. In some implementations, the GUI 1700 may include a main menu page 1710 with options 1720-1750 that provide various functions. For example, option 1720 may include functionality for tracking a user's own individual progress (e.g., as a bar chart 1722), option 1730 may include functionality for gamifying the user's progress (e.g., comparing a bar chart 1732 of the user with bar charts of other users 1734), option 1740 may include functionality for adjusting sensor settings, and option 1750 may include miscellaneous functionality. It is understood that these options are exemplary only, and other functionality may be provided.

In some implementations of the present disclosure, option 1720 may be configured to track a number of contractions/relaxations of a user's sphincter muscle, for example. In an implementation option 1720 may display the results in a bar chart 1722, with heights of each bar corresponding to magnitude or strength of set of contractions (one bar per contraction) or a number of contractions per session, day, etc.

In some implementations, option 1730 may be configured to track the contractions/relaxations or characteristics thereof (e.g., signal strength of the user), and compare those against other users or against a user's previous best performance, thus gamifying the performance of the user. In this way, the user may be incentivized to achieve progress towards a goal. For example, comparative charts 1732, 1734 may be displayed to illustrate performance differences between users.

In some implementations, option 1730 may be configured to show a user a pattern of contractions as a time series, and the user can be instructed to attempt to match the displayed pattern. The system can score the degree to which the user's muscle contraction pattern matches (in terms of timing and relative amplitude) that of the displayed pattern. This score, can also be compared with that of other users. Any sharing of data by a clinician or medical practice in this scenario, would be done in a HIPAA compliant manner to protect the privacy of the patient, while still providing a social and motivational experience for the user.

In some implementations, option 1740 can be used to control stimulation settings and stimulation protocols. In some implementations, the stimulation protocol begins with detecting which pair of electrodes detects a strongest contraction signal to determine the electrode pair that is most proximate the nerve to be stimulated. The stimulation signal is then applied to that pair of electrodes in the form of a train of low-amplitude square wave pulses.

According to some implementations, the miscellaneous functionality 1750 may include a summary of the user's performance 1752 (e.g., as a pie chart). The miscellaneous functionality 1750 may also identify areas for improvement 1754. The miscellaneous functionality 1750 may also track a progress 1756 of the user (e.g., extrapolate future performance prediction based on past performance). It is understood that various other miscellaneous functionalities may be implemented in miscellaneous functionality 1750 in addition to the above-described functions.

The techniques described herein may be implemented as method(s) that are performed by physical computing device (s); as one or more non-transitory computer-readable storage media storing instructions which, when executed by computing device(s), cause performance of the method(s); or, as physical computing device(s) that are specially configured with a combination of hardware and software that causes performance of the method(s).

Figure 18:
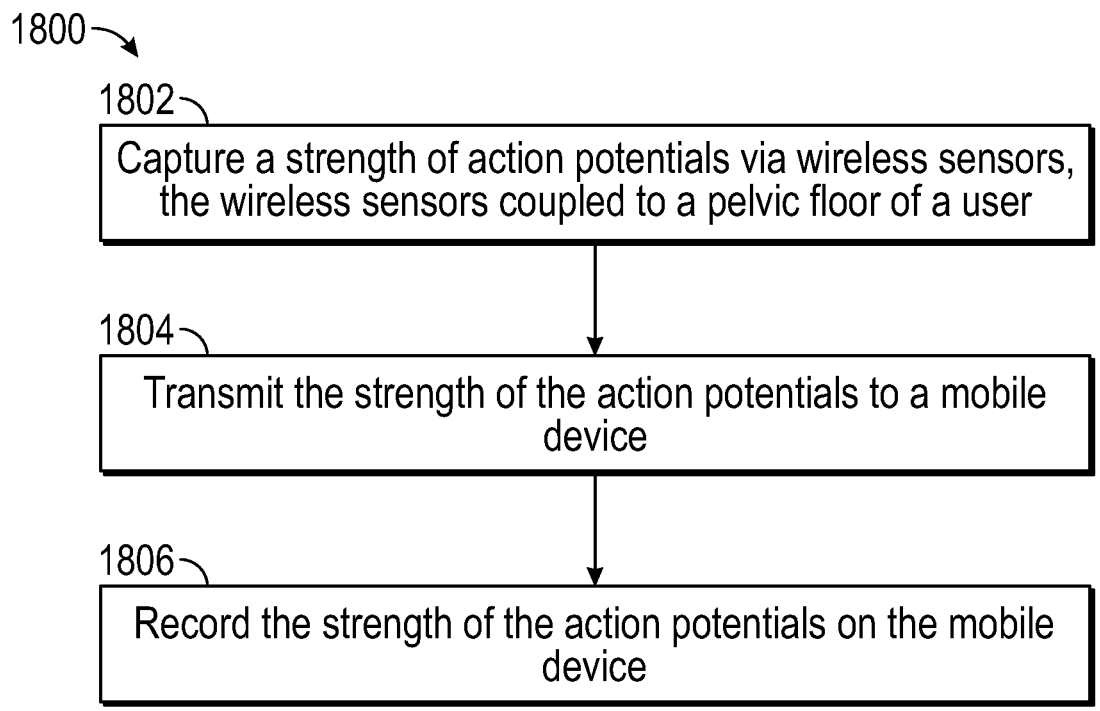
FIG. 18 illustrates an example flow diagram for pelvic floor feedback and neuromodulation according to some implementations.
Figure 19:
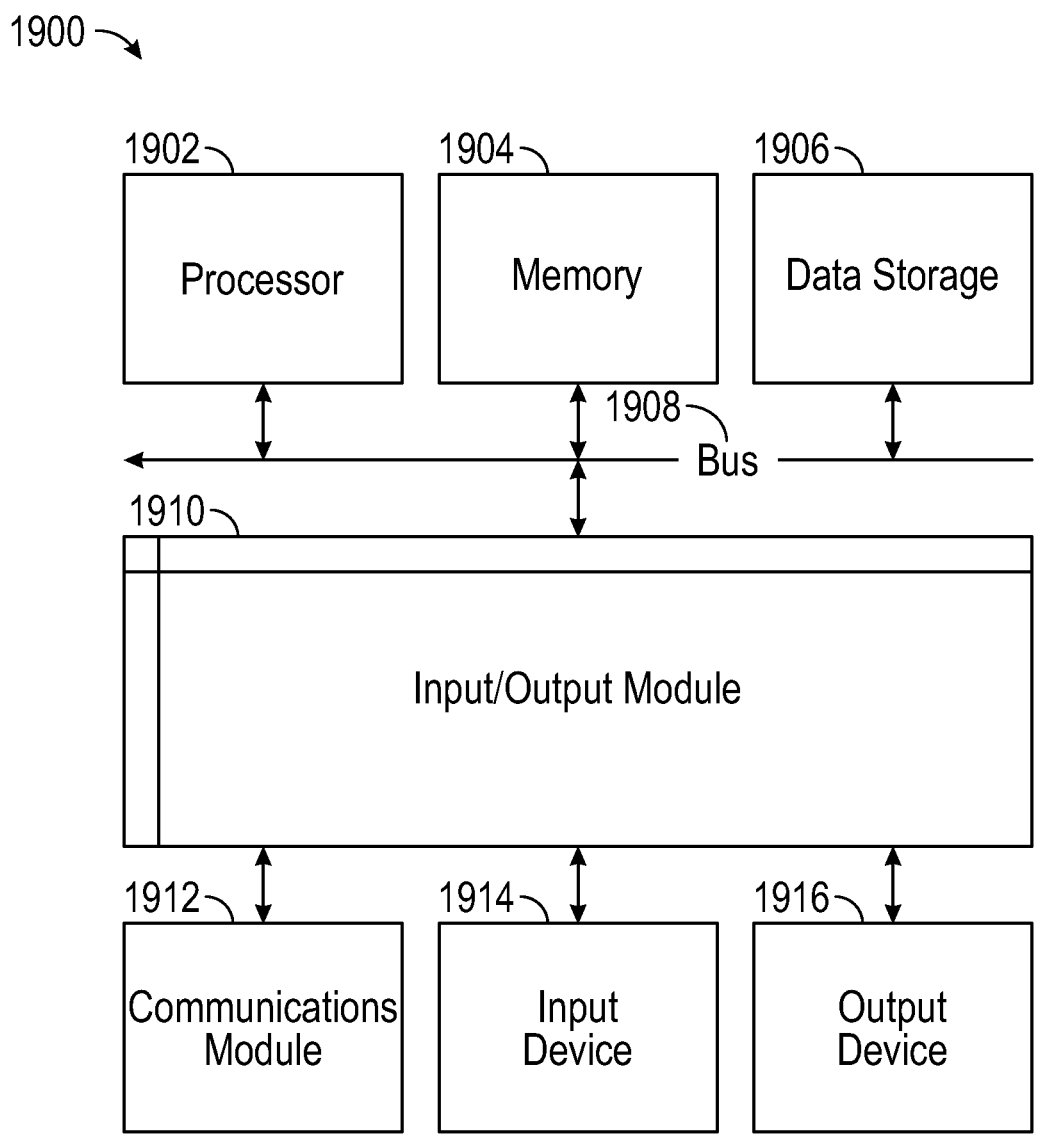
FIG. 19 is a block diagram illustrating an example computer system with which aspects of the subject technology may be implemented.

FIG. 18 illustrates an example flow diagram (e.g., process 1800) for pelvic floor feedback and neuromodulation according to some implementations. The example process 1800 may be implemented in relation to FIGS. 1-17. Further, for explanatory purposes, the blocks of the example process 1800 are described herein as occurring in series, or linearly. However, multiple blocks of the example process 1800 may occur in parallel. In addition, the blocks of the example process 1800 need not be performed in the order shown and/or one or more of the blocks of the example process 1800 need not be performed.

At block 1802, a strength of action potentials via wireless sensors is captured. The wireless sensors may be positioned proximate to a pelvic floor of a user. At block 1804, the strength of the action potentials is transmitted to a mobile device. At block 1806, the strength of the action potentials is recorded on the mobile device.

In some implementations of the present disclosure, the process 1800 may involve the same software system on the mobile device and software on a remote server that interacts with the software system, allowing the information gathered on the mobile device to be shared with the software on the remote server.

In some implementations of the present disclosure, the process 1800 may include storing the strength of the action potentials on either the mobile device or a remote server. In some implementations of the present disclosure, the process 1800 may include creating a game environment by the software system, with which the user may interact via controlled contractions and relaxations of the target muscle group.

In some implementations of the present disclosure, the process 1800 may include interacting with the remote server via the software system to allow the user to play with and against other users interacting via other mobile devices at sites remote to both the server and the user to create an online gaming environment.

Aspects of the present disclosure are useful for various purposes, including, but not limited to: urodynamics, rehabilitation for spinal cord injuries (e.g., bowel and bladder), sports training, counting the number of action potentials as a way to score points (e.g., weightlifting, interval training, and also as a way to weight train weightlessly), game controller for a video game console (e.g., such as NINTENDO WII), fatigue tracker for job health programs (e.g., a delivery worker and the amount of stress they put on their back).

Aspects of the present disclosure may also improve resident training programs by teaching patients to relax muscles, identifying what muscles they shouldn't be using when performing certain tasks, etc. (e.g., may be verified first and then used as normalized values to teach future patients). Additional health benefits may be experienced in constraint induced movement therapy (CIMT) for upper extremity rehab, tension headache, temporomandibular disorder (TMJ) pain, tortocollis, cerebral palsy, to reduce emotional decision making in financial traders (e.g., galvanic skin response, heart rate, muscle recruitment), pelvic floor dysfunction/chronic pelvic pain (e.g., for men and women), meditation training (e.g., wearing multiple garments simultaneously to relay what muscles groups to relax, etc.).

Aspects of the present disclosure may also be utilized for treating pediatric patients, men and women with urinary and fecal incontinence, pelvic pain, dyspareunia, vaginismus, constipation, and pregnant women, among others.

FIG. 1900 is a block diagram illustrating an exemplary computer system 1900 with which the devices and systems of the above-described Figures may be implemented. In certain aspects, the computer system 1900 may be implemented using hardware or a combination of software and hardware, either in a dedicated server, integrated into another entity, or distributed across multiple entities.

Computer system 1900 includes a bus 1908 or other communication mechanism for communicating information, and a processor 1902 coupled with bus 1908 for processing information. By way of example, the computer system 1900 may be implemented with one or more processors 1902. Processor 1902 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 1900 can include, in addition to hardware, code that creates an execution environment for the computer program in question, for example, code that constitutes processor firmware, a protocol stack, a database management system, an operating system, or a combination of one or more of them stored in an included memory 1904, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1908 for storing information and instructions to be executed by processor 1902. The processor 1902 and the memory 1904 can be supplemented by, or incorporated in, special purpose logic circuitry.

The instructions may be stored in the memory 1904 and implemented in one or more computer program products, i.e., one or more modules of computer program instructions encoded on a computer-readable medium for execution by, or to control the operation of, the computer system 1900, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multi-paradigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 1904 may also be used for storing temporary variable or other intermediate information during execution of instructions to be executed by processor 1902.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 1900 further includes a data storage device 1906 such as a magnetic disk or optical disk, coupled to bus 1908 for storing information and instructions. Computer system 1900 may be coupled via input/output module 1910 to various devices. The input/output module 1910 can be any input/output module. Exemplary input/output modules 1910 include data ports such as USB ports. The input/output module 1910 is configured to connect to a communications module 1912. Exemplary communications modules 1912 include networking interface cards, such as Ethernet cards and modems. In certain aspects, the input/output module 1910 is configured to connect to a plurality of devices, such as an input device 1914 and/or an output device 1916. Exemplary input devices 1914 include a keyboard and a pointing device, e.g., a mouse or a trackball, by which a user can provide input to the computer system 1900. Other kinds of input devices 1914 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback, and input from the user can be received in any form, including acoustic, speech, tactile, or brain wave input. Exemplary output devices 1916 include display devices such as an LCD (liquid crystal display) monitor, for displaying information to the user.

According to one aspect of the present disclosure, the devices and systems can be implemented using a computer system 1900 in response to processor 1902 executing one or more sequences of one or more instructions contained in memory 1904. Such instructions may be read into memory 1904 from another machine-readable medium, such as data storage device 1906. Execution of the sequences of instructions contained in the main memory 1904 causes processor 1902 to perform the process steps described herein. One or more processors in a multi-processing arrangement may also be employed to execute the sequences of instructions contained in memory 1904. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back-end component, e.g., such as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. The communication network can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 1900 can include clients and servers. A client and server are generally remote from each other and typically interact through a communication network. The relationship of client and server arises by virtue of computer programs running on the respective computers and having a client-server relationship to each other. Computer system 1900 can be, for example, and without limitation, a desktop computer, laptop computer, or tablet computer. Computer system 1900 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer-readable medium" as used herein refers to any medium or media that participates in providing instructions to processor 1902 for execution. Such a medium may take many forms, including, but not limited to, non-volatile media, volatile media, and transmission media. Non-volatile media include, for example, optical or magnetic disks, such as data storage device 1906. Volatile media include dynamic memory, such as memory 1904. Transmission media include coaxial cables, copper wire, and fiber optics, including the wires that comprise bus 1908. Common forms of machine-readable media include, for example, floppy disk, a flexible disk, hard disk, magnetic tape, any other magnetic medium, a CD-ROM, DVD, any other optical medium, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the terms "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

What is claimed is:

1. A device for electromyography (EMG)-based biofeedback-augmented pelvic floor muscle training by a user in need thereof, the device comprising:
   a. a housing comprising a pillow that is configured as a garment or a saddle;
   b. a plurality of sensor electrodes configured for detection of EMG signals generated by an anal sphincter muscle of the user in response to a voluntary contraction of the anal sphincter muscle by the user, the plurality of sensor electrodes coupled to the housing at locations for positioning the plurality of sensor electrodes adjacent to the anal sphincter muscle of the user when the housing is mounted or worn by the user;
   c. an EMG signal sensing and processing processor in functional communication with the plurality of sensor electrodes, wherein the EMG signal sensing and processing processor is configured to receive and interpret parameters of the EMG signals from the anal sphincter muscle generated in response to the voluntary contraction of the anal sphincter muscle of the user; and
   d. a control processor configured to transmit the parameters of the EMG signals to a remote user interface module,
wherein the pillow has a compression rate of 25% for an applied pressure of between 0.6 and 4.0 psi.

2. The device of claim 1, wherein the pillow is configured as a garment configured to be worn by the user.

3. The device of claim 1, wherein the plurality of sensor electrodes are arranged in a sensor electrode array comprising at least one opposing pair of sensor electrodes separated by a distance.

4. The device of claim 3, wherein the distance between the at least one opposing pair of sensor electrodes ranges from about 0.75" to about 1.5", or about 1.0".

5. The device of claim 3, wherein each sensor electrode of the plurality of sensor electrodes is between about 0.75" and 1.25", or about 1.0" wide.

6. The device of claim 1, wherein the plurality of sensor electrodes comprise at least one pair of elongated sensor electrodes arranged along a longitudinal axis of the housing.

7. The device of claim 6, wherein each sensor electrode in the at least one pair of elongated sensor electrodes is between about 3.5" to about 4.5" long, and between 0.75" and about 1.25' wide, and a distance between each sensor electrode in the least one pair of elongated sensor electrodes ranges from about 0.75" to about 1.5" or about 1.0".

8. The device of claim 1, wherein the plurality of sensor electrodes are included on a disposable flexible circuit comprising a polyethylene terephthalate (PET) substrate.

9. The device of claim 1, further comprising a ground electrode against which sensed electrical activity is compared to detect the generated EMG signals.

10. The device of claim 1, wherein the plurality of sensor electrodes comprise a ground electrode and at least one pair of elongated electrodes arranged along a longitudinal axis of the housing, wherein the plurality of sensor electrodes are arranged in a sensor electrode array comprising at least one opposing pair of sensor electrodes, wherein a distance between opposing sensor electrodes in the at least one opposing pair of sensor electrodes is about 1.0", wherein each electrode in the at least one pair of elongated electrodes is between about 3.5" to about 4.5" long, and between 0.75" and about 1.25" wide, and wherein the plurality of sensor electrodes are included on a disposable flexible circuit comprising a polyethylene terephthalate (PET) substrate.

11. The device of claim 1, wherein the parameters of the EMG signal comprise the amplitude, frequency, and phase of the EMG signal.

12. The device of claim 1, further comprising a power source, a voltage regulator, an EMG signal amplifier, a microprocessor associated memory for program storage and data storage, a pre-amplifier and analog-to-digital converter, a data transceiver, a patient isolation circuitry, a transmitter, or any combination thereof.

13. The device of claim 1, wherein the control processor further comprises a transmitter configured to transmit the parameters of the EMG signals to the remote user interface module.

14. The device of claim 13, wherein the transmitter is configured to communicate wirelessly through a Bluetooth Low Energy (BLE) device.

15. The device of claim 13, wherein the remote user interface module comprises a mobile device.

16. The device of claim 1, wherein the housing is configured to be mounted by the user.

17. A method for a user to train pelvic floor muscles using biofeedback, the method comprising:
   a. obtaining or having obtained a device of claim 1,
   b. wearing or mounting the device;
   c. performing controlled contractions and relaxations of the anal sphincter muscle by the user, wherein the device;
      i. detects EMG signals generated by the voluntary contraction of the anal sphincter muscle by the user
      ii. receives and interprets parameters of the detected EMG signals; and
      iii. transmits the parameters of the detected EMG signals to a remote computing device, wherein a remote user interface of the remote computing device provides feedback to the user; and
      iv. based on the transmitted detected EMG signal parameters, providing feedback to the user to:
         I. adjust the controlled contractions and relaxations of the anal sphincter muscle;
         II. adjusting placement of the device; or
         III. a combination thereof;
   d. based on the feedback provided by the device:
      i. adjusting the controlled contractions and relaxations of the anal sphincter muscle;
      ii. adjusting mounting of the device; or
      iii. combinations thereof.

18. A device for electromyography (EMG)-based biofeedback-augmented pelvic floor muscle training by a user in need thereof, the device comprising:
   a. a saddle configured to be mounted by the user;
   b. a disposable electrode sensor array comprising:
      i. a pair of opposing elongated sensor electrodes arranged along a longitudinal axis of the saddle, wherein each sensor electrode in the pair of opposing elongated sensor electrodes is between about 3.5" to about 4.5" long, and between 0.75" and about 1.25" wide, and a distance between the sensor electrodes in the pair of opposing elongated sensor electrodes ranges from about 0.75" to about 1.5" or about 1.0", and wherein the disposable electrode sensor array is included on a disposable flexible circuit comprising a polyethylene terephthalate (PET) substrate;

ii. a ground electrode against which sensed electrical activity is compared;
c. an EMG signal sensing and processing processor in functional communication with the sensor electrodes, wherein the EMG signal sensing and processing unit is configured to receive and interpret parameters of the EMG signals from an anal sphincter muscle of the user in response to voluntary contraction of the anal sphincter muscle by the user; and
d. a control processor configured to transmitting the parameters of the EMG signals to a remote user interface module.

* * * * *